United States Patent [19]

Keller

[11] Patent Number: 4,709,075

[45] Date of Patent: Nov. 24, 1987

[54] PREPARATION OF ALKYL N-MALEYLPHENYLALANATE

[75] Inventor: Reinhold Keller, Bad Soden am Taunus, Fed. Rep. of Germany

[73] Assignee: Hoechst Aktiengesellschaft, Frankfurt, Fed. Rep. of Germany

[21] Appl. No.: 805,618

[22] Filed: Dec. 6, 1985

[30] Foreign Application Priority Data

Dec. 8, 1984 [DE] Fed. Rep. of Germany ....... 3444915

[51] Int. Cl.$^4$ ............................................ C07C 67/313
[52] U.S. Cl. ....................................... 560/41; 562/450
[58] Field of Search ........................... 560/41; 562/450

[56] References Cited

U.S. PATENT DOCUMENTS

| | | | |
|---|---|---|---|
| 3,901,871 | 8/1975 | Anderson | 560/41 X |
| 4,507,231 | 3/1985 | Gourbault | 560/41 |
| 4,539,147 | 9/1985 | Filippini et al. | 560/41 |

*Primary Examiner*—Werren B. Lone
*Assistant Examiner*—Vera C. Clarke
*Attorney, Agent, or Firm*—Finnegan, Henderson, Farabow, Garrett & Dunner

[57] ABSTRACT

Alkyl N-maleylphenylalanate is prepared by reacting the starting material alkyl L-phenylalanate and maleic anhydride in aqueous solution at a pH of at most 7.5. The reaction products can be isomerized with dipolar aprotic solvents into the corresponding fumaric acid monoamides and thus can be used as an intermediate in the preparation of alkyl α-L-aspartyl-L-phenylalanate.

5 Claims, No Drawings

PREPARATION OF ALKYL N-MALEYLPHENYLALANATE

According to published Japanese Patent Application No. 49-42,491 (1974), alkyl α-L-aspartyl-L-phenylalanates which are suitable for use as sweeteners can be prepared by chemical or biochemical amination in the α-position from the corresponding alkyl fumarylmonophenylalanates. These fumaryl compounds are prepared by reacting fumaryl dichloride with at most equimolar amounts of alkyl phenylalanates in organic solvents, and subsequently hydrolyzing the corresponding monoacyl chlorides. In the case of methyl fumarylmono-L-phenylalanate the yield is at most 62%. The alkyl ester of fumaryldiphenylalanine should to be formed in only small amounts. Owing to the starting material fumaryl dichloride and the relatively low yield, this process is unsatisfactory.

It has now been found, surprisingly, that alkyl N-maleylphenylalanate can be isomerized into the corresponding fumaric acid derivative in very high yield. The monoamides of maleic acid are thus suitable for use as intermediates for preparing the corresponding fumaric acid monoamides. They can however also be converted directly into the corresponding aspartyl compounds by chemical or biochemical amination using methods known per se.

The invention thus concerns the use of the compound of the general formula I

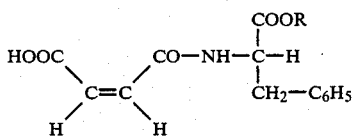

in which R denotes alkyl having 1 to 4 carbon atoms, for preparing the corresponding fumaric acid monoamides of the general formula II

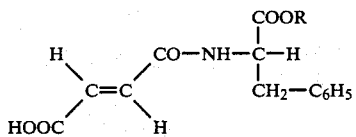

in which R has the abovementioned meaning, by isomerization.

Published Japanese Patent Application No. Sho 48-52,741 describes a process for preparing alkyl N-maleylphenylalanate by reacting alkyl L-phenylalanate and maleic anhydride at room temperature in an organic solvent. However, this reaction proceeds only in the presence of stoichiometric amounts of triethylamine and with an overall yield of 85%. The triethylamine used is lost as ammonium chloride and needs to be removed.

It has now been found that alkyl L-phenylalanates and maleic anhydride can also be made to react in aqueous solution, producing alkyl N-maleylphenylalanate in practically quantitative yield. This is particularly surprising insofar as in aqueous solution, in particular within the acid pH range, hydrolysis of the ester was expected.

The invention thus also concerns a process for preparing alkyl N-maleylphenylalanates of the general formula I, which comprises reacting alkyl L-phenylalanates of the general formula III

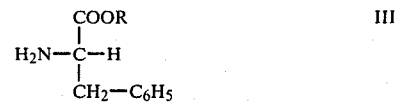

in which R is alkyl having 1 to 4 carbon atoms, with maleic anhydride in aqueous solution at a pH of at most 7.5.

The alkyl L-phenylalanate of the formula III which is preferably used is the methyl ester or the ethyl ester. The esters can be used in the free form and then be dispersed by thorough mixing in water. They are brought into solution by setting a pH within the range from about 3 to 7.5. It is more advantageous to use the ester of the formula III in the form of its salt, for example the hydrochloride, since the salts are more readily soluble. This solution then has added to it the maleic anhydride a little at a time, either continuously or at intervals. By addition of a suitable base, advantageously an alkali metal hydroxide solution such as sodium hydroxide solution, the pH is maintained within the stated range, advantageously at pH 6.0, since at that pH the reaction proceeds particularly rapidly and completely.

It is possible to use one of the two reactants in excess, for example the maleic anhydride. Since, however, the reaction proceeds rapidly and completely even with equimolar amounts, using excess amounts generally produces no benefits.

The maleic anhydride can be added in solid form or in solution. Water is a possible solvent, but preference is given to inert polar organic solvents, on the one hand to water-miscible solvents such as acetone and on the other to sparingly water-soluble solvents such as methyl isobutyl ketone, which can also be used for extracting the product.

The reaction can be effected within the range from about 0° to 50° C., advantageously at 10° to 40° C., in particular at room temperature.

After the reaction has ended, the product can be precipitated by acidification to a pH of 3 or below and/or be extracted with an organic solvent.

The products of the process are obtained in almost quantitative yield and high chemical and optical purity.

The isomerization to give the corresponding fumaric acid half-amides can be effected in the conventional manner, for example by heating in the presence of an acid catalyst, for example a mineral acid, it being necessary to arrange for appropriate precautions so as to prevent, for example, hydrolysis of the ester or other secondary reactions. It is particularly advantageous to carry out the isomerization in inert dipolar aprotic liquids of the type described in British Patent No. 1,246,349. With this method of isomerization, the compound of the formula I can be in solution in the inert dipolar aprotic solvent or be used as solution in some other solvent, for example in a nonpolar organic solvent. Such a solution in a nonpolar organic solvent can be for example the extract (dried if necessary) of the compound of the formula I from the reaction medium. For the particulars, see said British Patent No. 1,246,349.

The alkyl fumarylmono-L-phenylalanate ester thus prepared can then be converted into the alkyl α-L-aspartyl-L-phenylalanate ester.

The examples which follow illustrate the invention in more detail.

EXAMPLE 1

Preparation of methyl N-maleyl-L-phenylalanate 215 g (1 mol) of methyl L-phenylalanate hydrochloride are dissolved in 1 liter of water, and the solution is brought to pH 6.0 by addition of 5N sodium hydroxide solution. 98 g (1 mol) of pulverized maleic anhydride are added, with stirring, a little at a time while the pH of the reaction solution is maintained at 6.0 by addition of 5N sodium hydroxide solution. After addition is complete, stirring is continued for a further 10 minutes, and the solution is then brought to pH 3.0 or less with concentrated hydrochloric acid. The product, which is precipitated in the form of an oil, is taken up in diethyl ether, and the solution is dried with magnesium sulfate and concentrated. This gives 271 g (98% of theory) of colorless crystals having a melting point of 90° C.

Specific angle of rotation: $[\alpha]_D^{25} + 148.9$ (c=2, CHCl$_3$).

|  | C | H | N | % |
|---|---|---|---|---|
| calculated: | 60.6 | 5.5 | 5.1 |  |
| found: | 60.3 | 5.3 | 5.1 |  |

The same method can also be used to prepare the other lower alkyl esters, for example the ethyl ester.

EXAMPLE 2

Preparation of methyl N-fumaryl-L-phenylalanate 50 g of the N-maleyl half-amide obtained in Example 1 are taken up in 200 ml of xylene and 10 ml of dimethylformamide and are refluxed for 8 hours. The solution is cooled down to room temperature, and the crystals which precipitate are filtered off and washed with diethyl ether. This gives 48 g (96% of theory) of colorless crystals having a melting point of 153° C.

Specific angle of rotation: $[\alpha]_D^{25} + 56.1$ (c=2, CHCl$_3$).

The same method can also be used to isomerize the other lower alkyl esters.

What is claimed is:

1. A process for preparing the compounds of the formula I

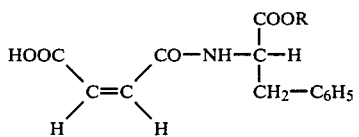

which comprises reacting alkyl L-phenylalanates of the formula III

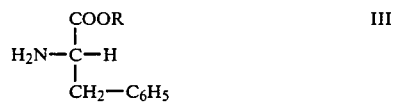

in which R is alkyl having 1 to 4 carbon atoms, in aqueous solution at 0° to 50° C. within the pH range from 3 to 7.5 with maleic anhydride.

2. The process as claimed in claim 1 wherein R is methyl or ethyl.

3. The process as claimed in claim 1, wherein the reaction is carried out at 10° to 40° C.

4. The process as claimed in claim 1, wherein the alkyl L-phenylalanate ester is used in the form of its salts.

5. The process as claimed in claim 4, wherein the alkyl L-phenylalanate ester is used in the form of its hydrochloride.

* * * * *